US011041154B2

(12) United States Patent
Kiani et al.

(10) Patent No.: US 11,041,154 B2
(45) Date of Patent: Jun. 22, 2021

(54) CRISPR FLUORESCENT GUIDE RNA (FGRNA) TO UNDERSTANDING GRNAS EXPRESSED FROM POL II PROMOTORS

(71) Applicant: Arizona Board of Regents on behalf of Arizona State University, Scottsdale, AZ (US)

(72) Inventors: Samira Kiani, Scottsdale, AZ (US); Xiao Wang, Chandler, AZ (US); David Menn, Tempe, AZ (US); Mo Reza Ebrahimkhani, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 16/632,792

(22) PCT Filed: Sep. 29, 2017

(86) PCT No.: PCT/US2017/054271

§ 371 (c)(1),
(2) Date: Jan. 21, 2020

(87) PCT Pub. No.: WO2019/017988

PCT Pub. Date: Jan. 24, 2019

(65) Prior Publication Data

US 2020/0377884 A1 Dec. 3, 2020

Related U.S. Application Data

(60) Provisional application No. 62/535,499, filed on Jul. 21, 2017.

(51) Int. Cl.
*C12N 15/113* (2010.01)
*C12N 9/22* (2006.01)
*C12N 15/63* (2006.01)

(52) U.S. Cl.
CPC .............. *C12N 15/113* (2013.01); *C12N 9/22* (2013.01); *C12N 15/63* (2013.01); *C12N 2310/15* (2013.01); *C12N 2310/16* (2013.01); *C12N 2310/20* (2017.05); *C12N 2310/3519* (2013.01)

(58) Field of Classification Search
None
See application file for complete search history.

(56) References Cited

U.S. PATENT DOCUMENTS

| | | | |
|---|---|---|---|
| 9,664,676 | B2 | 5/2017 | Jaffrey |
| 2015/0141282 | A1 | 5/2015 | Jaffrey et al. |
| 2016/0208243 | A1 | 7/2016 | Zhang et al. |
| 2017/0022499 | A1 | 1/2017 | Lu et al. |

FOREIGN PATENT DOCUMENTS

| | | | |
|---|---|---|---|
| WO | 2016183402 | A2 | 11/2015 |
| WO | 2016054106 | A1 | 4/2016 |
| WO | 2019005851 | A1 | 1/2019 |
| WO | 2019005853 | A2 | 1/2019 |
| WO | 2019005856 | A1 | 1/2019 |
| WO | 2019018041 | A1 | 1/2019 |
| WO | 2019237124 | A1 | 12/2019 |

OTHER PUBLICATIONS

Bassett, A. R., et al. Highly Efficient Targeted Mutagenesis of *Drosophila* with the CRISPR/Cas9 System. Cell Rep. 4, 220-228 (2013).
Chavez, A. et al. Highly efficient Cas9-mediated transcriptional programming. Nat. Methods 12, 326-328 (2015).
Ferré-D'Amaré, A. R., et al. (1998). Crystal structure of a hepatitis delta virus ribozyme. Nature, 395(6702), 567.
Filonov, G. S., et al. Broccoli: Rapid Selection of an RNA Mimic of Green Fluorescent Protein by Fluorescence-Based Selection and Directed Evolution. J. Am. Chem. Soc. 136, 16299-16308 (2014).
Fu, Y., et al. Improving CRISPR-Cas nuclease specificity using truncated guide RNAs. Nat. Biotechnol. 32, 279-284 (2014).
Gao, Y. et al. Self-processing of ribozyme-flanked RNAs into guide RNAs in vitro and in vivo for CRISPR-mediated genome editing: Self-processing of ribozyme-flanked RNAs into guide RNAs. J. Integr. Plant Biol. 56, 343-349 (2014).
Haft, D. H., et al. "A guild of 45 CRISPR-associated (Cas) protein families and multiple CRISPR/Cas subtypes exist in prokaryotic genomes." PLoS computational biology 1.6 (2005): e60.
Hwang, W. Y. et al. Efficient genome editing in zebrafish using a CRISPR-Cas system. Nat. Biotechnol. 31, 227-229 (2013).
International Searching Authority, International Search Report and Written Opinion for application PCT/US2017/054271, dated Dec. 27, 2017.
Kiani, S. et al. CRISPR transcriptional repression devices and layered circuits in mammalian cells. Nat. Methods 11, 723-726 (2014).
Ma, H. et al. Multiplexed labeling of genomic loci with dCas9 and engineered sgRNAs using CRISPRainbow. Nat. Biotechnol. 34, 528-530 (2016).
Ma, M., et al. A Guide RNA Sequence Design Platform for the CRISPR/Cas9 System for Model Organism Genomes. BioMed Res. Int. 2013, e270805 (2013).
Malina, A. et al., "Repurposing CRISPR/Cas9 for in situ functional assays", Genes & Development, Dec. 2013, vol. 27, No. 23, pp. 2602-2614 DOI:doi: 10.1101/gad.227132.113.
Miao, J. et al. Targeted mutagenesis in rice using CRISPR-Cas system. Cell Res. 23, 1233-1236 (2013).
Nissim, L., et al. Multiplexed and Programmable Regulation of Gene Networks with an Integrated RNA and CRISPR/Cas Toolkit in Human Cells. Mol. Cell 54, 698-710 (2014).

(Continued)

*Primary Examiner* — Nancy J Leith
(74) *Attorney, Agent, or Firm* — Quarles & Brady LLP

(57) ABSTRACT

Provided herein are tools for understanding and engineering dynamics of synthetic genetic circuits which utilize CRISPR components. More particularly, methods, systems, and compositions for directing Cas9 activity using a fluorescent guide RNA (fgR-NA) which fluoresces in the presence of small molecules (e.g., DFHBI-IT) are described and illustrated in the present provisional application.

12 Claims, 6 Drawing Sheets

Specification includes a Sequence Listing.

(56) References Cited

OTHER PUBLICATIONS

Paige, J. S. et al., “RNA mimics of green fluorescent protein,” Science 333: 642-646 (2011).
Paige, J. S., et al. Fluorescence Imaging of Cellular Metabolites with RNA. Science 335, 1194-1194 (2012).
Pley, H. W., et al. (1994). Three-dimensional structure of a hammerhead ribozyme. Nature, 372(6501), 68.
Przybilski, R. et al. Csy4 is responsible for CRISPR RNA processing in Pectobacterium atrosepticum. RNA Biol. 8, 517-528 (2011).
Shechner, D. M., et al. Multiplexable, locus-specific targeting of long RNAs with CRISPR-Display. Nat. Methods 12, 664-670 (2015).
Xie, K., et al. Boosting CRISPR/Cas9 multiplex editing capability with the endogenous tRNA-processing system. Proc. Natl. Acad. Sci. 112, 3570-3575 (2015).
Zalatan, J. G. et al. Engineering Complex Synthetic Transcriptional Programs with CRISPR RNA Scaffolds. Cell 160, 339-350 (2015).
U.S. Appl. No. 16/626,013, Kiani et al., filed Dec. 23, 2019.
U.S. Appl. No. 16/626,016, Kiani et al., filed Dec. 23, 2019.
U.S. Appl. No. 16/626,021, Kiani et al., filed Dec. 23, 2019.

CRISPR FLUORESCENT GUIDE RNA (FGRNA) TO UNDERSTANDING GRNAS EXPRESSED FROM POL II PROMOTORS

CROSS-REFERENCE TO RELATED APPLICATIONS

This application represents the national stage entry of PCT International Application No. PCT/US2017/054271, filed on Sep. 29, 2017, and claims the benefit of U.S. Provisional Application Ser. No. 62/535,499, filed on Jul. 21, 2017, which is incorporated by reference herein as if set forth in its entirety.

STATEMENT REGARDING FEDERALLY SPONSORED RESEARCH

This invention was made with government support under RO1 GM106081 awarded by the National Institutes of Health. The government has certain rights in the invention.

BACKGROUND

Clustered Regularly Interspaced Short Palindromic Repeat (CRISPR) technology has become a staple of the field of synthetic biology, with such diverse applications as induced mutagenesis, insertion/deletion for silencing genes, gene activation and repression, and genome labeling. This is due in a large part to the technology's specificity, ease of design, and modularity.

The CRISPR system consists of a guide RNA (gRNA) and the protein Cas9. When coexpressed, the gRNA and Cas9 complex with each other, and the gRNA targets Cas9 to a specific sequence of DNA through complementary base-pairing with a ~20 nucleotide region on the 5' end of the gRNA. There are few reliable, non-invasive methods by which gRNA expression levels can be measured. Those that do exist are indirect, such as activating or repressing a downstream fluorescent gene, and are obfuscated by complex gRNA/Cas9 and gRNA/DNA interactions. Accordingly, there remains a need for direct, non-invasive methods for understanding the dynamics of genetic circuits which utilize CRISPR components.

SUMMARY

Provided herein are tools for understanding and engineering dynamics of synthetic genetic circuits which utilize CRISPR components. More particularly, systems, methods, and compositions for directing Cas9 activity using a fluorescent guide RNA (fgRNA) which fluoresces in the presence of small molecules (e.g., DFHBI-1T).

In a first aspect, provided herein is a method of directly detecting and measuring gRNA expression in a cell. The method can comprise or consist essentially of (a) introducing a synthetic regulatory system into the cell, the synthetic regulatory system comprising: (i) a nucleotide sequence encoding an inactivated Cas nuclease; and (ii) a fluorescent guide RNA (fgRNA) operably linked to a CRISPR-responsive promoter, the fgRNA comprising a fluorophore-binding RNA aptamer sequence; and a 20-nucleotide (nt) spacer sequence that hybridizes with a target sequence of a DNA molecule in a eukaryotic cell that contains the DNA molecule; and (b) contacting the cell comprising the synthetic regulatory system to a small molecule inducer of the fluorophore binding RNA aptamer; wherein gRNA expression is measured by fluorescence monitoring. The CRISPR-responsive promoter can be a RNA Pol II promoter. The RNA Pol II promoter can be doxycycline inducible. The fgRNA can be configured for ribozyme-mediated editing, Csy4-mediated editing, or tRNA-mediated editing. The fluorophore binding RNA aptamer sequence can be selected from the group consisting of a Broccoli aptamer, Spinach aptamer, and Spinach2 aptamer. The small molecule inducer can be DFHBI-1T. The fluorophore RNA aptamer sequence can be selected from the group consisting of SEQ ID NO:1. SEQ ID NO:2, and SEQ ID NO:3.

In another aspect, provided herein is a method of monitoring efficiency of CRISPR-mediated gene repression. The method can comprise or consist essentially of (a) introducing a synthetic regulatory system into the cell, the synthetic regulatory system comprising: (i) a nucleotide sequence encoding an inactivated Cas nuclease; and (ii) a fluorescent guide RNA (fgRNA) operably linked to a CRISPR-responsive promoter, the fgRNA comprising a fluorophore-binding RNA aptamer sequence; and a 20-nucleotide (nt) spacer sequence that hybridizes with a target sequence of a DNA molecule in a eukaryotic cell that contains the DNA molecule; and (b) contacting the cell comprising the synthetic regulatory system to a small molecule inducer of the fluorophore binding RNA aptamer; wherein gRNA expression is measured by fluorescence monitoring. The CRISPR-repressible promoter can be a doxycycline inducible RNA Pol II promoter. The fgRNA can be configured for ribozyme-mediated editing, Csy4-mediated editing, or tRNA-mediated editing. The fluorophore binding RNA aptamer sequence can be selected from the group consisting of a Broccoli aptamer, Spinach aptamer, and Spinach2 aptamer. The small molecule inducer can be DFHBI-1T. The fluorophore RNA aptamer sequence can be selected from the group consisting of SEQ ID NO:1. SEQ ID NO:2, and SEQ ID NO:3.

In a further aspect, provided herein is a synthetic regulatory system where the system comprises or consists essentially of (i) a nucleotide sequence encoding a Cas nuclease; and (ii) a fluorescent guide RNA (fgRNA) operably linked to a CRISPR-responsive promoter. The fgRNA can comprise a fluorophore-binding RNA aptamer sequence, and a 20-nucleotide (nt) spacer sequence that hybridizes with a target gene sequence of a DNA molecule in a eukaryotic cell that contains the DNA molecule. The CRISPR-repressible promoter can be a doxycycline inducible RNA Pol II promoter. The RNA Pol II promoter can be doxycycline inducible. The fgRNA can be configured for ribozyme-mediated editing, Csy4-mediated editing, or tRNA-mediated editing. The fluorophore-binding RNA aptamer sequence can be selected from the group consisting of a Broccoli aptamer, Spinach aptamer, and Spinach2 aptamer. The small molecule inducer can be DFHBI-1T. The fluorophore RNA aptamer sequence can be selected from the group consisting of SEQ ID NO: 1. SEQ ID NO:2, and SEQ ID NO:3.

In another aspect, provided herein is a fluorescent guide RNA (fgRNA) operably linked to a CRISPR-responsive promoter, the fgRNA comprising a fluorophore-binding RNA aptamer sequence; and a 20-nucleotide (nt) spacer sequence that hybridizes with a target sequence of a DNA molecule in a eukaryotic cell that contains the DNA molecule. The fgRNA can be configured for ribozyme-mediated editing, Csy4-mediated editing, or tRNA-mediated editing. The fluorophore-binding RNA aptamer sequence can be selected from the group consisting of a Broccoli aptamer, Spinach aptamer, and Spinach2 aptamer. The fluorophore RNA aptamer sequence can be selected from the group consisting of SEQ ID NO: 1. SEQ ID NO:2, and SEQ ID NO:3.

Figure 1A:
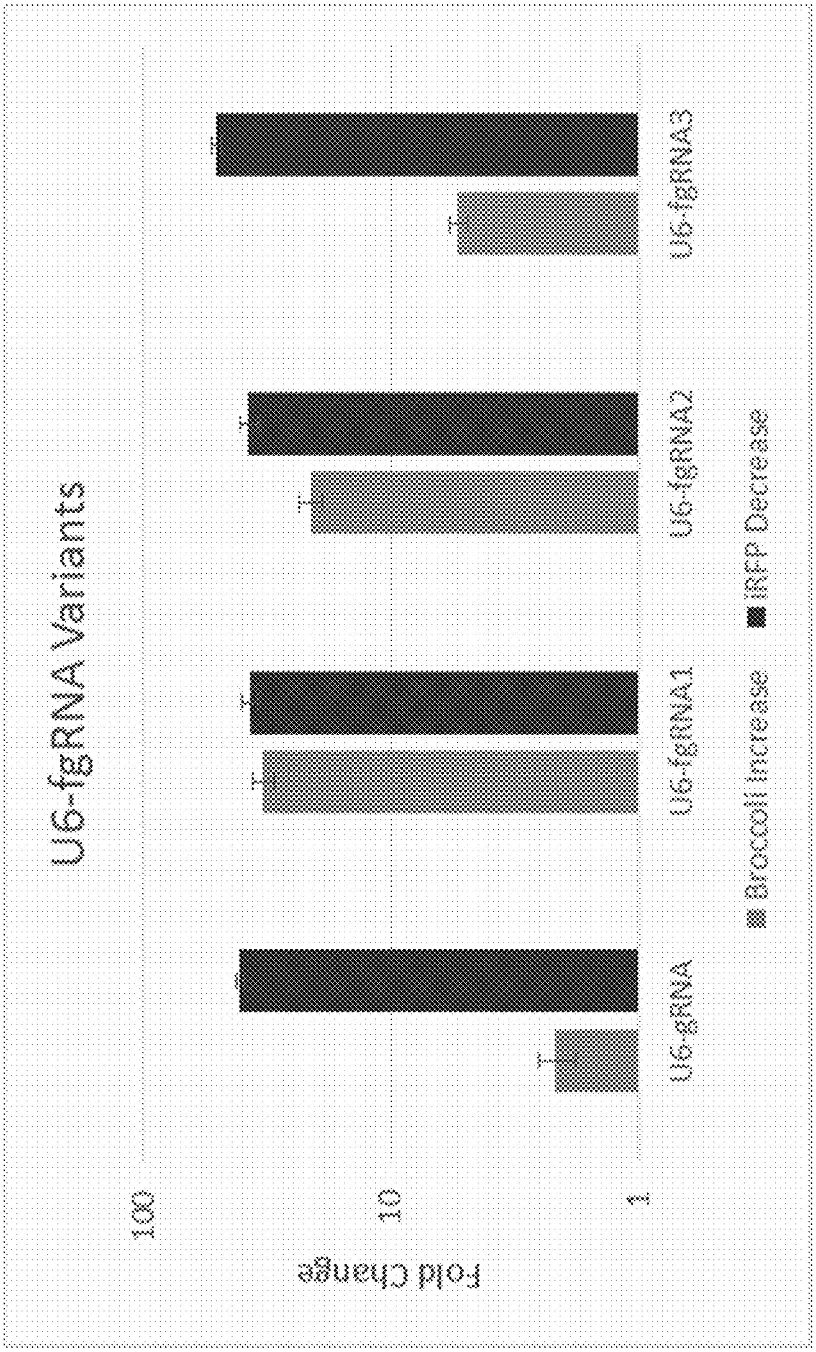
FIGS. 1A-1C presents flow cytometry data. (A) Pol III driven fgRNA functionality with the Broccoli sequence inserted into varying parts of the gRNA sequence. (B) Pol III driven fgRNA functionality when paired with 3 different post-transcriptional editing methods: ribozyme-guide-ribozyme (RGR), Csy4-guide-Csy4 (CGC), and tRNA-guide-tRNA (TGT). (C) fgRNA functionality as assayed by fluorescence expression when fgRNA is driven by a doxycycline-inducible Pol II (TRE) promoter and post-transcriptionally edited by different methods. All data are the mean of geometric means of 4 replicates±standard deviation.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The compositions and methods described herein are based at least in part on the inventors' development of a nucleic acid construct capable of selectively directing Cas9 activity and fluorescing in the presence of a small molecule, and which permits direct, non-invasive measurement of CRISPR gRNA expressed from various promoters including RNA Pol II promoters.

In a first aspect, therefore, provided herein is a guide RNA construct comprising a fluorophore-binding nucleic acid aptamer. Useful nucleic acid aptamers have the capacity to bind to a small molecule dye whose fluorescence is switched on upon binding the RNA. In this manner, the nucleic acid aptamer binds selectively to conditionally fluorescent molecules ("fluorophores").

Any appropriate fluorophore-binding nucleic acid aptamer can be used according to the methods and systems described herein. Preferably, the fluorophore binding nucleic acid aptamer is the broccoli aptamer. When the small molecule DFHBI-1T is introduced to cells cultured in a growth medium, it permeates the cell membranes, binds to the broccoli aptamer, and fluoresces green. As described in U.S. Pat. No. 9,664,676 (which is hereby incorporated by reference in its entirety), the core sequence element of an aptamer that induces the fluorescence of the fluorophore DFHBI-1T has been identified to be, as follows: GAGANG-GUCGGGUCCAGN-N-GCUGUNGAGUAGAGU-GUGGGCUC (SEQ ID NO:4), where N at each of positions 5, 18, and 25 can be any single nucleotide base (A, U, G, or C), and N at position 19 can be any single nucleotide base (A, U, G, or C) or an insertion of any length of various nucleotide bases. Numerous sequences of different lengths have been placed at position 19 and the resulting aptamer retained fluorescence. The core can also be preceded or followed by any arbitrary sequence, but the core is needed for fluorescence.

Other fluorophore binding nucleic acid aptamers that can be used include, without limitation, Spinach and Spinach2 (Paige et al., "RNA mimics of green fluorescent protein," Science 333: 642-646 (2011), which is hereby incorporated by reference in its entirety), Baby Spinach, and "Bunch of Baby Spinach" (BoBS) aptamers (Shechner et al., *Nature Methods* 12, 664-670 (2015)). The small molecule fluorophore ligand ("inducer") for these aptamers is DFHBI-1T. In certain embodiments, the guide RNA construct is configured to direct Cas9 activity and to fluoresce in the presence of the small molecule DFHBI-1T. As used herein, the term "aptamer" refers to nucleic acid molecules and encompasses nucleic acid molecules that bind specifically to small molecule fluorophores and are useful for in vitro or in vivo monitoring of the activity, trafficking or localization, degradation, or quantification of various molecules. In addition to the methods described and exemplified herein, any conventional method for imaging, visualizing, or quantifying fluorescent molecules can be used in accordance with this disclosure.

Nucleotide sequences of three exemplary fgRNA variants are listed below:

fgRNA1:
(SEQ ID NO: 1)
NNNNNNNNNNNNNNNNNNNNGTTTGAGAGCTAGCGCAGACGG
TCGGGTCCAGATATTCGTATCTGTCGAGTAGAGTGTGGGCTG
CGCTAGCAAGTTCAAATAAGGCTAGTCCGTTATCAACTTGAA
AAAGTGGCACCGAGTCGGTGC fgRNA2:
(SEQ ID NO: 2)
NNNNNNNNNNNNNNNNNNNNGTTTGAGAGCTAGAAATAGCAA
GTTCAAATAAGGCTAGTCCGTTATCAACTTGCGCAGACGGTC
GGGTCCAGATATTCGTATCTGTCGAGTAGAGTGTGGGCTGCG
CAAGTGGCACCGAGTCGGTGC fgRNA3:
(SEQ ID NO: 3)
NNNNNNNNNNNNNNNNNNNNGTTTGAGAGCTAGAAATAGCAA
GTTCAAATAAGGCTAGTCCGTTATCAACTTGCGCAGACGGTC
GGGTCCAGATATTCGTATCTGTCGAGTAGAGTGTGGGCTGCG
CAAGTGGCACCGAGTCGGTGC

The sequence in bold font is the 20nt gRNA target sequence. This sequence will vary depending on the particular application. The underlined sequence is a broccoli aptamer sequence. Editing sequences can be placed directly on either side of the full fgRNA sequence. If no editing is needed, the transcriptional start is preferably placed as close to the beginning of the fgRNA sequence as possible, and the terminator is preferably located immediately after the fgRNA sequence.

Eukaryotes utilize three nuclear enzymes, Pol I, II, and III, to synthesize different classes of RNA, of which the Pol II transcription machinery is the most complex. RNA polymerase II promoters, which constitute the majority of the characterized promoters, cannot be directly used for gRNA production in vivo because the 5' CAP, possible 5'/3' UTR, and the poly A tail may hinder guide RNA function. Additionally, RNAs transcribed by RNA polymerase II are rapidly exported from the nuclei into the cytosol while nuclear localization is required for the CAS9/gRNA duplex to access the genomic DNA. Thus, the RNAs transcribed by RNA polymerase II are physically separated from the intended targets that are located in the nucleus. Consequently, guide RNAs for in vivo assays are usually expressed under promoters transcribed by RNA polymerase III (e.g., U6 promoter).

As described herein, however, fluorescent guide RNAs (fgRNAs) can be expressed under a RNA Pol II promoter such as a tetracycline response element (TRE) promoter using any number of different mRNA editing strategies. While gRNA is typically produced by RNA Polymerase III (Pol III) in eukaryotic cells, editing mRNA into fgRNA allows the production of fgRNA from RNA Polymerase II (Pol II) promoters as well. This greatly expands the contexts in which this technology can be utilized.

In some cases, CRISPR-responsive promoters are used. As used herein, the term "CRISPR-responsive promoter" encompasses eukaryotic promoters as well as synthetic gene regulatory devices and circuits for regulated gene expression. In some embodiments, a CRISPR-responsive promoter comprises a RNA Pol II promoter or an RNA Pol II promoter. The CRISPR-responsive promoter can be a CRISPR-repressible promoter (CRP) or a CRISPR-activatable promoter (CAP). A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb).

In certain embodiments, it may be advantageous to use a cell type-specific promoter to drive expression of a fgRNA provided herein. For example, a CRISPR-based genetic circuit may be configured to comprise a cell type-specific promoter in place of a synthetic promoter to drive fgRNA expression in a spatially controlled manner.

In some cases, the self-cleaving ribozyme is Csy4, a CRISPR-associated endonuclease which recognizes and cleaves a unique 28-nt RNA sequence. When this sequence is placed on either side of a gRNA within an mRNA transcript and expressed, Csy4 efficiently cleaves gRNAs sandwiched between 28-nt Csy4 recognition sites to produce a functional gRNA. If Csy4 is not expressed, the gRNA is not released, adding temporal and/or spatial control to the system. In some cases, the Csy4 endonuclease is derived from *Pseudomonas aeruginosa.*

In other cases, the RGR motif is composed of a gRNA flanked by a 5' Hammerhead (HH) type ribozyme (Pley et al., *Nature* 372, 1994), which cleaves directly before the first nucleotide of the gRNA, and a 3' Herpes Delta Virus (HDV) ribozyme (Ferre-D'Amare et al., *Nature* 395: 567-74, 1998), which cleaves directly after the last gRNA nucleotide. When a gRNA sequence is flanked by these two self-cleaving ribozymes, the resulting gRNA is nearly indistinguishable from those produced from a Pol III promoter. By way of example, an RNA molecule can be designed to comprise a HH type ribozyme at the 5'-end, a fgRNA as described herein, and a HDV ribozyme at the 3'-end.

tRNA-mediated editing is achieved by inserting tRNA sequences into the mRNA transcript on either side of the gRNA. Endogenous tRNA cleaving enzymes RNase P and RNase Z cleave on the 5' and 3' sides of the tRNA, respectively. In some cases, flanking editing sequences are included on either side of a fgRNA.

Figure 1B:
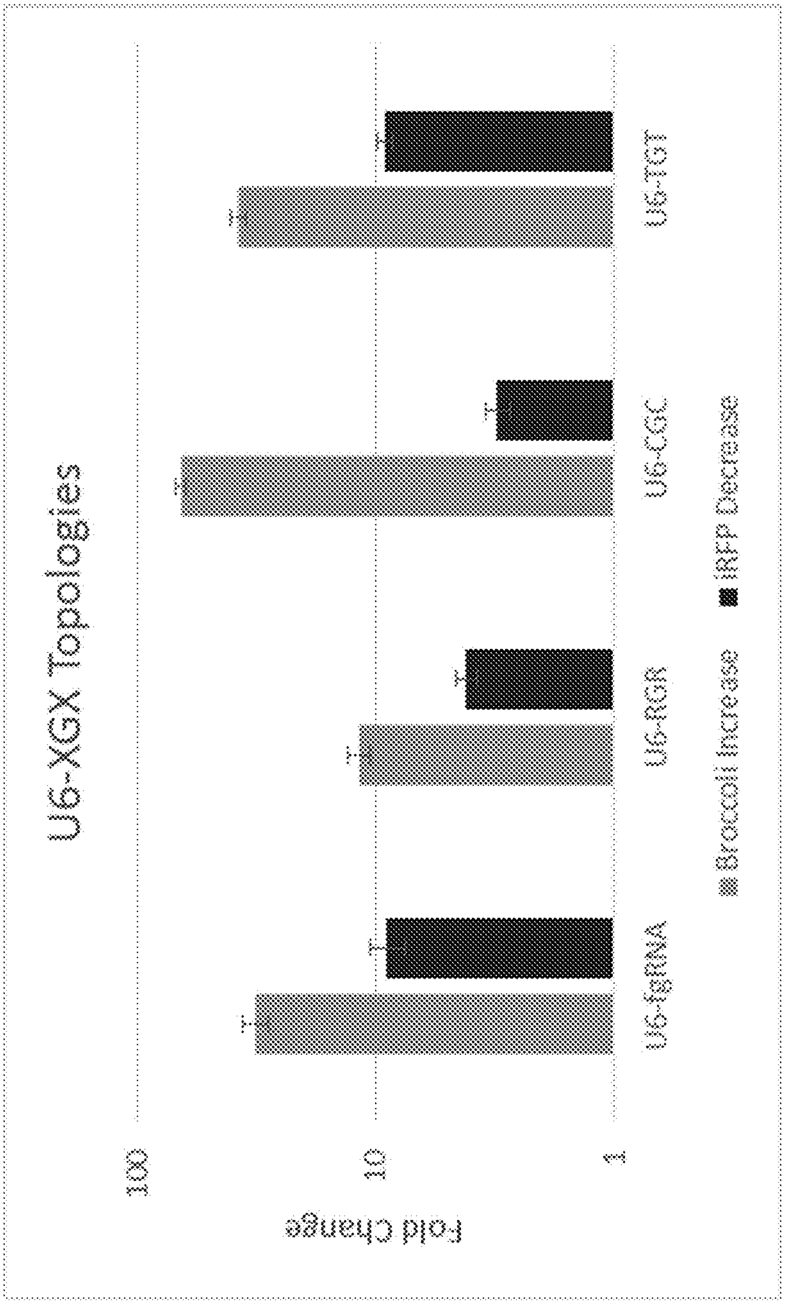
Figure 1C:
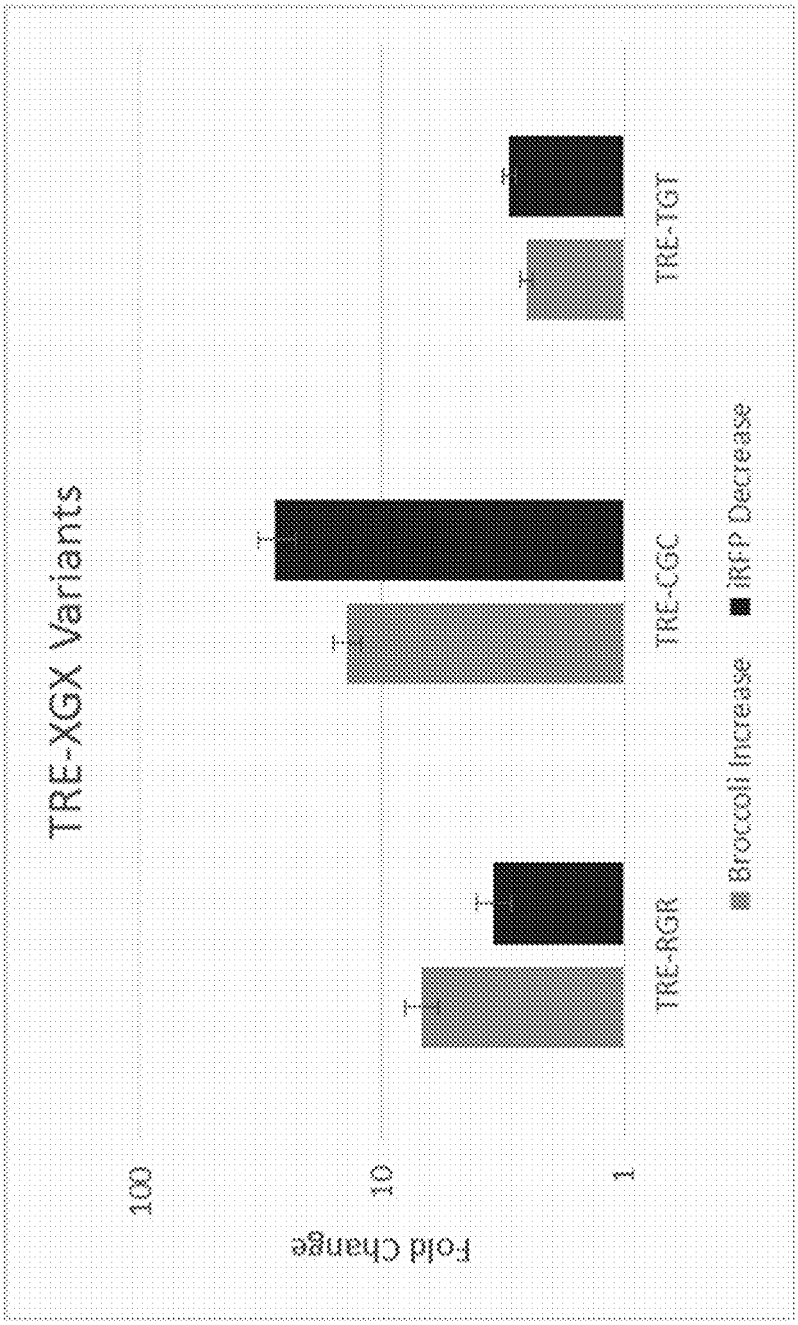
Figure 2A:
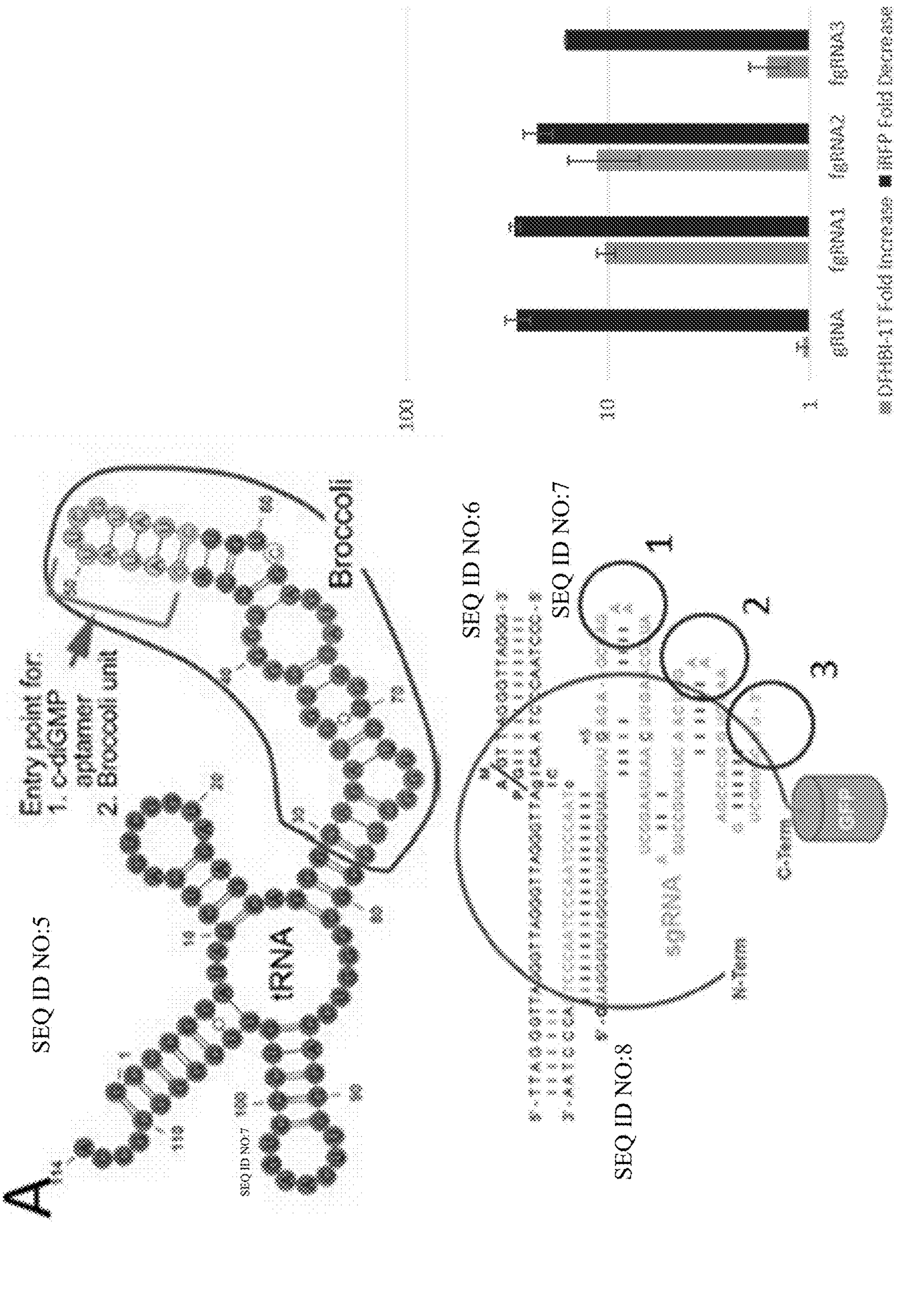
FIGS. 2A-2C. (A) Fluorescent RNA apatamer Broccoli and its three potential insertions sites within the gRNA (top). Flow cytometry data (bottom) indicate that insertion into the "1" position has no effect on gRNA repression strength and is detectably green. (B) A comparison of three common methods of editing a long RNA transcript into a gRNA using a U6 (pol III) promoter: topologies (top) and their cleavage locations (arrows) and flow cytometry results (bottom). Addition of flanking editor sequences has a measureable impact on gRNA repression. (C) Initial pol II gRNA expression efficiency in a simple repressor circuit. Topology (top) and flow cytometry results (bottom). All flow cytometry is the mean of four replicates±SD.
Figure 2B:
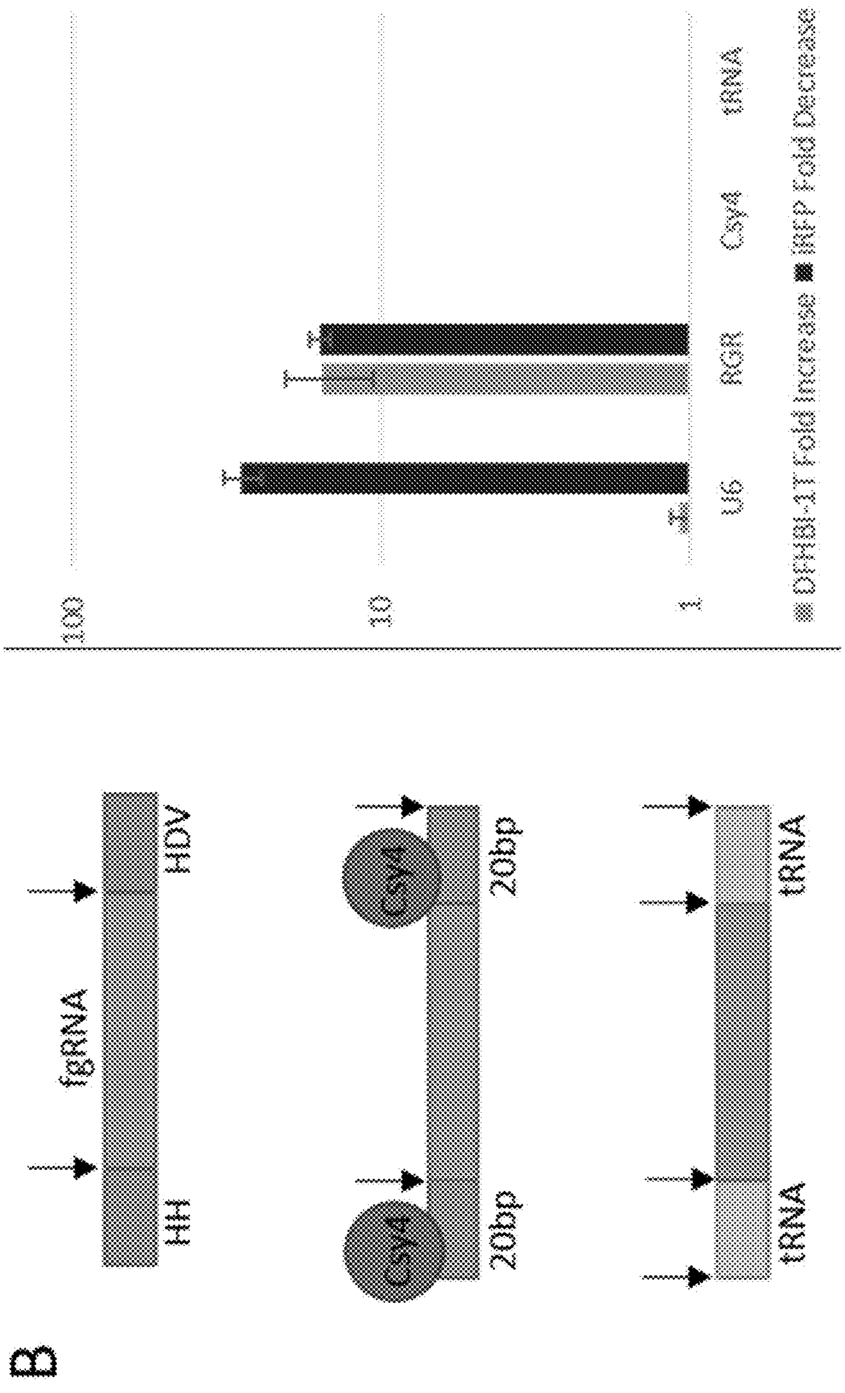
Figure 2C:
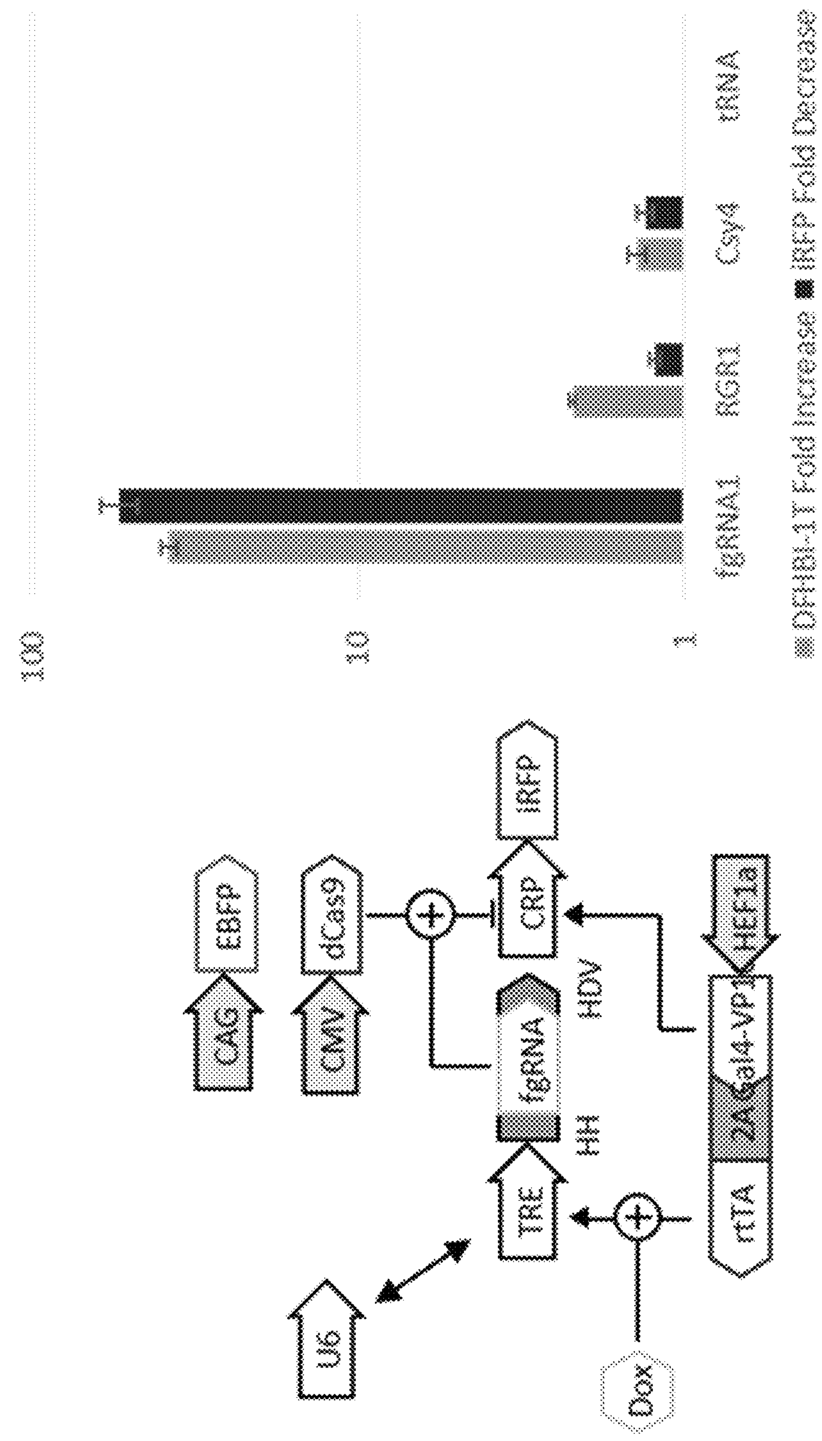

Referring to FIG. 1*b*, three different RNA editing strategies were assayed: editing by the Csy4 protein (CGC), ribozyme-guide-ribozyme (RGR) motif, and endogenous tRNA machinery (TGT). Using fgRNA1 (see FIG. 1A), we compared the efficiency of repression by U6 driven fgRNAs edited by the Csy4 protein (CGC), ribozyme-guide-ribozyme (RGR) motif, or endogenous tRNA machinery (TGT). Our data demonstrate that gRNAs can be efficiently produced in vitro and in vivo from essentially any promoter when the primary transcripts are flanked by self-cleaving ribozymes. Referring to FIG. 1*c*, repression of Infrared Fluorescent Protein (iRFP) by TRE driven RGR-edited, Csy4-edited, and tRNA-edited fgRNAs was detected, but the level of expression and efficiency of repression was lower than that of a U6-driven fgRNA construct.

fgRNAs described herein can be used with any CRISPR-based system. CRISPR systems belong to different classes, with different repeat patterns, sets of genes, and species ranges. A CRISPR enzyme is typically a type I or III CRISPR enzyme. In some cases, a fgRNA is used with a CRISPR system derived from a type II CRISPR system. The type II CRISPR enzyme may be any Cas enzyme. The terms "Cas" and "CRISPR-associated Cas" are used interchangeably herein. The Cas enzyme can be any naturally-occurring nuclease as well as any chimeras, mutants, homologs, or orthologs. In some embodiments, one or more elements of a CRISPR system is derived from a particular organism comprising an endogenous CRISPR system, such as *Streptococcus pyogenes* (SP) CRISPR systems or *Staphylococcus aureus* (SA) CRISPR systems. The CRISPR system is a type II CRISPR system and the Cas enzyme is Cas9 or a catalytically inactive Cas9 (dCas9). Other non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. A comprehensive review of the Cas protein family is presented in Haft et al. (2005) Computational Biology, *PLoS Comput. Biol.* 1:e60. At least 41 CRISPR-associated (Cas) gene families have been described to date.

It will be understood that the CRISPR-Cas system for use with a fgRNA described herein is non-naturally occurring in a cell, i.e. engineered or exogenous to the cell. The CRISPR-Cas system as referred to herein has been introduced in a cell. Methods for introducing the CRISPR-Cas system in a cell are known in the art. In some cases, the cell comprises one or more engineered nucleic acid molecules encoding individual components of the CRISPR-Cas system, which are expressed in the cell to establish a functional CRISPR complex, capable of modifying (such as cleaving) a target DNA sequence.

So that the methods and systems provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, the terms "synthetic" and "engineered" are used interchangeably and refer to the aspect of having been manipulated by the hand of man.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

The section below describes a RNA construct capable of (i) directing Cas9 activity and (ii) fluorescing in the presence of the small molecule DFHBI-1T. Here, we demonstrate that this construct allows direct, non-invasive measurement of the CRISPR gRNA, which was not previously possible. In addition, we demonstrate expression of the fgRNA construct from RNA Pol III and Pol II promoters.

We engineered a fluorophore-binding RNA aptamer within gRNAs. We chose "Broccoli" aptamer due to its brightness and short sequence. The small molecule DFHBI-1T permeates cell membranes, binds to Broccoli aptamer, and fluoresces green. A gRNA sequence has regions into which additional sequences can be inserted while retaining its ability to complex with Cas9 and target DNA (e.g., stem loop 1, stem loop 2, and 3' end). We inserted Broccoli into these regions of a gRNA driven by a Pol III (U6) promoter and examined whether this modification altered gRNA functionality by indirectly measuring Cas9/gRNA-mediated repression of an infra-red fluorescent protein (iRFP) driven by our previously reported CRISPR-responsive promoter (CRP).

After inserting Broccoli into the indicated regions of a gRNA driven by Pol III (U6) promoter, we examined whether these modifications altered gRNA functionality using indirect measurement of Cas9/gRNA-mediated repression of an infra-red fluorescent protein (iRFP) driven by a CRISPR-responsive promoter (CRP). Flow cytometry data demonstrate that Broccoli containing fluorescent gRNAs are functional to a level comparable with unmodified gRNAs (FIG. 1*a*).

After observing that the fluorescent gRNA (fgRNA) with Broccoli in stem loop 1 (fgRNA1) functioned best, we further modified this gRNA design with three previously published strategies to edit gRNA post-transcriptionally. We generated fgRNAs flanked by ribozymes (RGR), flanked by the RNA endonuclease Csy4 target sites (CGC), and flanked by tRNA sequence (TGT).

fgRNA Sequences: The nucleotide sequences of the three variants of the fgRNA are as follows:

fgRNA1:
(SEQ ID NO: 1)
NNNNNNNNNNNNNNNNNNNNGTTTGAGAGCTAGCGCAGACGG
TCGGGTCCAGATATTCGTATCTGTCGAGTAGAGTGTGGGCTG
CGCTAGCAAGTTCAAATAAGGCTAGTCCGTTATCAACTTGAA
AAAGTGGCACCGAGTCGGTGC fgRNA2:
(SEQ ID NO: 2)
NNNNNNNNNNNNNNNNNNNNGTTTGAGAGCTAGAAATAGCAA
GTTCAAATAAGGCTAGTCCGTTATCAACTTGCGCAGACGGTC
GGGTCCAGATATTCGTATCTGTCGAGTAGAGTGTGGGCTGCG
CAAGTGGCACCGAGTCGGTGC fgRNA3:
(SEQ ID NO: 3)
NNNNNNNNNNNNNNNNNNNNGTTTGAGAGCTAGAAATAGCAA
GTTCAAATAAGGCTAGTCCGTTATCAACTTGAAAAAGTGGCA
CCGAGTCGGTGCGCGCAGACGGTCGGGTCCAGATATTCGTAT
CTGTCGAGTAGAGTGTGGGCTGCGC

The sequence in bold font is the 20nt gRNA target sequence. This sequence will vary depending on the particular application. The underlined sequence is the broccoli aptamer sequence. Editing sequences can be placed directly on either side of the full fgRNA sequence. If no editing is needed, the transcriptional start is preferably placed as close to the beginning of the fgRNA sequence as possible, and the terminator is preferably located immediately after the fgRNA sequence.

To study the functionality of these designs, we repeated flow cytometry experiments, demonstrating that modified fgRNAs are still functional (FIG. 1*b*). To show the feasibility of our approach in direct assessment of gRNAs expression from Pol II promoters, we engineered CGC, RGR, and TGT under TRE promoter and examined fgRNA expression (as indicated by Broccoli fluorescence level), and functionality (as indicated by iRFP decrease) by flow cytometry in the presence/absence of doxicycline (FIG. 1*c*). Our data demonstrate that fgRNAs enable direct measurement of gRNAs expression and functionality from Pol II promoters.

Data Collection Methods: HEK293ft cells were transfected with plasmids comprising a simple repressor circuit in amounts shown in Table 1. dCas9 and guide RNA (gRNA) complex to repress the expression of infrared fluorescent protein (iRFP). dCas9 was fused with BFP, functioning as a transfection marker, allowing us to disregard untransfected cells in the analysis. An activator construct co-expressed reverse tetracycline trans-activator (rtTA) and Ga14-VP16. rtTA complexes with Doxycycline to drive TRE (pol II) guide expression, while Ga14-VP16 drives iRFP expression in the absence of repression. Csy4 was added only to conditions which required editing by the Csy4 protein. Total mass was normalized to 600 ng using a non-coding, empty plasmid.

TABLE 1

Mass of plasmids used in transfections.

| | |
|---|---|
| dCas9-BFP | 75 |
| Activator | 20 |
| CRP-iRFP | 20 |
| Csy4 | 50* |
| Repressor | 100 |
| Empty | to 600ng |

All transfections were performed with PEI, using standard procedures and a 2:1 PEI:DNA ratio. Cell medium was changed every 24 hours. Flow cytometry was performed after 72 hours using a BD FACSCelesta (Becton Dickson) flow cytometer. Flow cytometry data were analyzed using FlowJo (FlowJo, LLC) software. To analyze the data, cells were first gated by Front Scatter (FSC) and Side Scatter (SSC) to eliminate non-cell events. Identified cells were then gated by BFP in order to remove non-transfected cells. From the remaining population of transfected cells, the geometric mean of BB515 (green fluorescence) and APC-Cy7 (infrared fluorescence) was calculated for 4 replicates of all conditions. These geometric mean values were then used to calculate fold changes between guide/no guide (for Pol III, U6 conditions) or between doxicycline/no doxicycline (for Pol II, TRE conditions). The results are presented in FIGS. 1A-1C and FIGS. 2A-2C.

What is claimed is:

1. A method of detecting guide RNA (gRNA) expression in a cell, the method comprising:
- (a) introducing a synthetic regulatory system into the cell, the synthetic regulatory system comprising
  - a fluorescent guide RNA (fgRNA) operably linked to a CRISPR-responsive promoter, the fgRNA comprising
    - a sequence selected from the group consisting of SEQ ID NO:1, SEQ ID NO:2, and SEQ ID NO:3, wherein the N nucleotides in each of SEQ ID NOs:1-3 are a 20-nucleotide (nt) spacer sequence that hybridizes with a target sequence of a DNA molecule in the cell;

and
- (b) contacting the cell comprising the synthetic regulatory system with a small molecule dye that fluoresces when bound to the fgRNA; and
- (c) monitoring the fluorescence of the small molecule dye to indicate gRNA expression.

2. The method of claim 1, wherein the CRISPR-responsive promoter is a RNA Pol II promoter.

3. The method of claim 2, wherein the RNA Pol II promoter is doxycycline inducible.

4. The method of claim 2, wherein the synthetic regulatory system further comprises cleavage targets flanking the fgRNA, wherein the cleavage targets are targeted using ribozyme-mediated editing, Csy4-mediated editing, or tRNA-mediated editing.

5. The method of claim 1, wherein the small molecule dye is DFHBI-1T.

6. The method of claim 1, wherein the synthetic regulatory system further comprises a nucleotide sequence encoding a Cas nuclease.

7. A synthetic regulatory system comprising a fluorescent guide RNA (fgRNA) operably linked to a CRISPR-responsive promoter, the fgRNA comprising a sequence selected from the group consisting of SEQ ID NO:1, SEQ ID NO:2, and SEQ ID NO:3, wherein the N nucleotides in each of SEQ ID NOs: 1-3 are a 20-nucleotide (nt) spacer sequence that hybridizes with a target gene sequence of a DNA molecule in a cell.

8. The system of claim 7, wherein the CRISPR-responsive promoter is a RNA Pol II promoter.

9. The system of claim 8, wherein the RNA Pol II promoter is doxycycline inducible.

10. The system of claim 7, wherein the synthetic regulatory system further comprises cleavage targets flanking the fgRNA, wherein the cleavage targets are targeted using ribozyme-mediated editing, Csy4-mediated editing, or tRNA-mediated editing.

11. The synthetic regulatory system of claim 7 further comprising a nucleotide sequence encoding a Cas nuclease.

12. A fluorescent guide RNA (fgRNA)

encoded by a nucleotide sequence selected from the group consisting of SEQ ID NO:1, SEQ ID NO:2, and SEQ ID NO:3, wherein the N nucleotides in each of SEQ ID NOs:1-3 are a 20-nucleotide (nt) spacer sequence that hybridizes with a target sequence of a DNA molecule in a cell.

* * * * *

SEQUENCE LISTING

<160> NUMBER OF SEQ ID NOS: 8

<210> SEQ ID NO 1
<211> LENGTH: 147
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: n is a, c, g, t or u

<400> SEQUENCE: 1
nnnnnnnnnn nnnnnnnnnn gtttgagagc tagcgcagac ggtcgggtcc agatattcgt 60
atctgtcgag tagagtgtgg gctgcgctag caagttcaaa taaggctagt ccgttatcaa 120
cttgaaaaag tggcaccgag tcggtgc 147

<210> SEQ ID NO 2
<211> LENGTH: 147
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: n is a, c, g, t or u

<400> SEQUENCE: 2
nnnnnnnnnn nnnnnnnnnn gtttgagagc tagaaatagc aagttcaaat aaggctagtc 60
cgttatcaac ttgcgcagac ggtcgggtcc agatattcgt atctgtcgag tagagtgtgg 120
gctgcgcaag tggcaccgag tcggtgc 147

<210> SEQ ID NO 3
<211> LENGTH: 151
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(20)
<223> OTHER INFORMATION: n is a, c, g, t or u

<400> SEQUENCE: 3
nnnnnnnnnn nnnnnnnnnn gtttgagagc tagaaatagc aagttcaaat aaggctagtc 60
cgttatcaac ttgaaaaagt ggcaccgagt cggtgcgcgc agacggtcgg gtccagatat 120
tcgtatctgt cgagtagagt gtgggctgcg c 151

<210> SEQ ID NO 4
<211> LENGTH: 42
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u -continued

```
<220> FEATURE:
<221> NAME/KEY: misc_feature
<222> LOCATION: (19)..(19)
<223> OTHER INFORMATION: n can be A, U, G, C or an insertion of any
      length of various nucloetide bases
<220> FEATURE:
<221> NAME/KEY: misc_feature
<222> LOCATION: (25)..(25)
<223> OTHER INFORMATION: n is a, c, g, or u

<400> SEQUENCE: 4

gaganggucg gguccagnng cugungagua gagugugggc uc                        42


<210> SEQ ID NO 5
<211> LENGTH: 114
<212> TYPE: DNA
<213> ORGANISM: Artificial Sequence
<220> FEATURE:
<223> OTHER INFORMATION: synthetic

<400> SEQUENCE: 5

gcccggauag cucagucggu agagcagcgg agacggucgg guccagauau ucguaucugu     60

cgaguagagu gugggcuccg cggguccagg guucaagucc cuguucgggc gcca          114


<210> SEQ ID NO 6
<211> LENGTH: 42
<212> TYPE: DNA
<213> ORGANISM: Artificial Sequence
<220> FEATURE:
<223> OTHER INFORMATION: synthetic

<400> SEQUENCE: 6

ttagggttag ggttagggtt agggttaggg ttagggttag gg                        42


<210> SEQ ID NO 7
<211> LENGTH: 42
<212> TYPE: DNA
<213> ORGANISM: Artificial Sequence
<220> FEATURE:
<223> OTHER INFORMATION: synthetic

<400> SEQUENCE: 7

ccctaaccct aaccctaacc ctaaccctaa ccctaaccct aa                        42


<210> SEQ ID NO 8
<211> LENGTH: 99
<212> TYPE: RNA
<213> ORGANISM: Artificial Sequence
<220> FEATURE:
<223> OTHER INFORMATION: synthetic

<400> SEQUENCE: 8

guaggguuag gguuaggguu aguuugagag cuagaaauag caaguucaaa uaaggcuagu     60

ccguuaucaa cuugaaaaag uggcaccgag ucggugcuu                            99
```